US007683162B2

(12) United States Patent
Gutman et al.

(10) Patent No.: US 7,683,162 B2
(45) Date of Patent: Mar. 23, 2010

(54) PROCESS OF PREPARING A CRYSTALLINE AZITHROMYCIN MONOHYDRATE

(75) Inventors: Daniella Gutman, Rishon Lezion (IL); Lea Shachal, Ahuzat Barak (IL)

(73) Assignee: Taro Pharmaceutical Industries Limited, Haifa Bay (IL)

( * ) Notice: Subject to any disclaimer, the term of this patent is extended or adjusted under 35 U.S.C. 154(b) by 65 days.

(21) Appl. No.: 11/211,011

(22) Filed: Aug. 24, 2005

(65) Prior Publication Data

US 2006/0063725 A1 Mar. 23, 2006

Related U.S. Application Data

(60) Provisional application No. 60/605,621, filed on Aug. 30, 2004.

(51) Int. Cl.
*C07H 17/08* (2006.01)
(52) U.S. Cl. ...................................... 536/7.4
(58) Field of Classification Search ................. None
See application file for complete search history.

(56) References Cited

U.S. PATENT DOCUMENTS

| | | | |
|---|---|---|---|
| 2,864,817 A | 12/1958 | Croley | |
| 4,474,768 A | 10/1984 | Bright | |
| 4,517,359 A | 5/1985 | Kobrehel et al. | |
| 5,869,629 A | 2/1999 | Bayod Jasanda et al. | |
| 5,958,888 A | 9/1999 | Macy et al. | |
| 6,013,778 A | 1/2000 | Heggie et al. | |
| 6,239,112 B1 | 5/2001 | Macy et al. | |
| 6,245,903 B1 | 6/2001 | Karimian et al. | |
| 6,268,489 B1 | 7/2001 | Allen et al. | |
| 6,365,574 B2 | 4/2002 | Singer et al. | |
| 6,420,537 B1 | 7/2002 | Bosch et al. | |
| 6,451,990 B1 | 9/2002 | Bayod Jasanada et al. | |
| 6,586,576 B2 | 7/2003 | Aronhime et al. | |
| 6,703,372 B1 | 3/2004 | Centellas et al. | |
| 2001/0047089 A1 | 11/2001 | Aronhime et al. | |
| 2002/0007049 A1 | 1/2002 | Singer et al. | |
| 2002/0111318 A1 | 8/2002 | Rengaraju | |
| 2004/0014952 A1 | 1/2004 | Rengaraju | |
| 2004/0043944 A1 | 3/2004 | Li et al. | |
| 2004/0043945 A1 | 3/2004 | Li et al. | |
| 2004/0053862 A1 | 3/2004 | Centellas et al. | |

FOREIGN PATENT DOCUMENTS

| | | |
|---|---|---|
| CN | 93120880.7 | 12/1993 |
| CN | ZL 94119821.9 | 3/1997 |
| EP | 0 879 823 A1 | 11/1998 |
| EP | 0 941 999 A2 | 9/1999 |
| EP | 0 984 020 A2 | 3/2000 |
| EP | 1 103 558 A2 | 5/2001 |
| WO | WO 00/27856 | 5/2000 |
| WO | WO 01/00640 A1 | 1/2001 |
| WO | WO 01/87912 A1 | 11/2001 |
| WO | WO 02/10181 A1 | 2/2002 |
| WO | WO 02/15842 A2 | 2/2002 |
| WO | WO 02/085898 A1 | 10/2002 |
| WO | WO 02/094843 A1 | 11/2002 |
| WO | WO 03/082889 A1 | 10/2003 |
| WO | WO 03/102009 A1 | 12/2003 |
| WO | WO 2004/035063 A1 | 4/2004 |

OTHER PUBLICATIONS

Gandhi, et al "Characterization of Azithromycin Hydrates" ( E. J. of Pharmaceutical Sciences) 2002, 16: 175-184.

*Primary Examiner*—Elli Peselev
(74) *Attorney, Agent, or Firm*—Venable LLP; Michael A. Gollin; Keith G. Haddaway

(57) ABSTRACT

The present invention provides a process of preparing a crystalline azithromycin monohydrate. The process involves dissolving azithromycin in a solution containing ethanol, adding the dissolved azithromycin into water to precipitate the crystals, isolating and drying the precipitate to a water content of about 5% (w/w) to about 7% (w/w). The resulting azithromycin monohydrate is stable, exhibiting less than 2% degradation, and non-hydroscopic.

7 Claims, 2 Drawing Sheets

PROCESS OF PREPARING A CRYSTALLINE AZITHROMYCIN MONOHYDRATE

CROSS REFERENCE TO RELATED APPLICATIONS

This application claims the benefit under 35 U.S.C. § 1.119 (e) of Provisional Application Ser. No. 60/605,621, filed Aug. 30, 2004.

FIELD OF THE INVENTION

The present invention relates to a process of preparing a crystalline azithromycin monohydrate.

BACKGROUND OF THE INVENTION

Azithromycin (9-deoxo-9a-aza-9a-methyl-9a-homoerythromycin A; CAS # 83905-01-5) is an antibiotic that interferes with protein synthesis in bacteria by binding to the 50S ribosomal subunit. Azithromycin is often used to treat respiratory infections, and is marketed under the tradename ZITHROMAX® (Pfizer Inc., New York, N.Y.). Azithromycin has the following chemical structure:

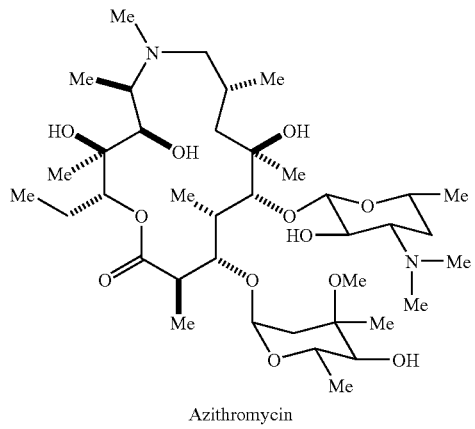

Azithromycin

At least two crystalline forms of azithromycin have been reported, azithromycin dihydrate and azithromycin monohydrate. U.S. Pat. No. 6,268,489 (the '489 patent) discloses azithromycin dihydrate as a crystalline form of azithromycin that contains two molecules of water per molecule of azithromycin. The '489 patent further describes that azithromycin dihydrate is stable and non-hygroscopic. Because of these properties, azithromycin dihydrate is used commercially. The '489 patent discloses azithromycin monohydrate as a crystalline form of azithromycin that contains one molecule of water per molecule of azithromycin. The '489 patent further states that azithromycin monohydrate is unstable and hygroscopic.

U.S. Publication No. 2004/0053862 A1 (the '862 publication) discloses an azithromycin monohydrate form having a water content from 4.0 to 6.0% w/w of water that is stable and non-hygroscopic. In the '862 publication, azithromycin monohydrate is prepared by the addition of an alkaline solution to a hydrochloric acid (HCl) solution of azithromycin; howver, it should be noted that azithromycin is reported to be unstable under acidic conditions (See, e.g., U.S. Pat. No. 6,586,576 B2).

There is a continuing need for a process of preparing crystalline azithromycin monohydrate that is useful for commercial purposes. It is desirable to prepare a crystalline azithromycin monohydrate that is substantially free of organic solvents and is stable, i.e., does not degrade.

SUMMARY OF THE INVENTION

A process for preparing crystalline azithromycin monohydrate that is substantially free of organic solvents and is stable, i.e., does not degrade, is described. The process comprises: (i) dissolving azithromycin in a first solution comprising at least about 50% (v/v) of a $C_1$-$C_6$ alcohol; (ii) adding the dissolved azithromycin to a second solution comprising at least about 50% (v/v) water to form a precipitate; (c) isolating the precipitate; and, (d) drying the isolated precipitate to a water content of about 5% (w/w) to about 7% (w/w). In one embodiment, the $C_1$-$C_6$ alcohol is ethanol; in another embodiment, the ethanol is a 95% (v/v) solution. The second solution may comprise water 100% (v/v). Crude azithromycin may be used for the crystallization.

The precipitate which is isolated in step (c) may be slurried in a solvent containing water prior to isolation and drying. The dissolved azithromycin formed in step (a) may be filtered. Filtration may be performed using diatomaceous earth. In one embodiment, the isolated crystalline azithromycin monohydrate has an ethanol content of less than 0.1%. The crystalline azithromycin monohydrate prepared by the process of this invention is characterized by having: (i) less than 2% (w/w) degradation after storage for at least about 3 months at 40° C. and 75% relative humidity; (ii) less than 5% change in the water content after storage for at least about 3 months at 40° C. and 75% relative humidity; or (iii) an ethanol content of less than 0.1%.

Dissolution of the azithromycin in step (a) may be performed at a temperature of about 50° C. to about the reflux temperature of the first solution. Precipitation of the dissolved azithromycin in step (c) may be performed at a temperature of about 0° C. to about 30° C. In another embodiment, step (c) may be performed at a temperature of about 20° C.

The precipitated crystalline azithromycin monohydrate may be isolated by filtration (step (d)). After isolation, the precipitate is dried to a water content of about 5% (w/w) to about 6.5% (w/w). In another embodiment, the isolated precipitate is dried to a water content of about 5% (w/w) to about 6% (w/w).

The crystalline azithromycin monohydrate prepared by the process of the invention exhibits: (i) an X-ray powder diffraction pattern substantially the same as that shown in FIG. 1; or (ii) a near infrared (NIR) spectrum substantially the same as that shown in FIG. 2.

BRIEF DESCRIPTION OF THE DIAGRAMS

DETAILED DESCRIPTION OF THE INVENTION

Figure 1:
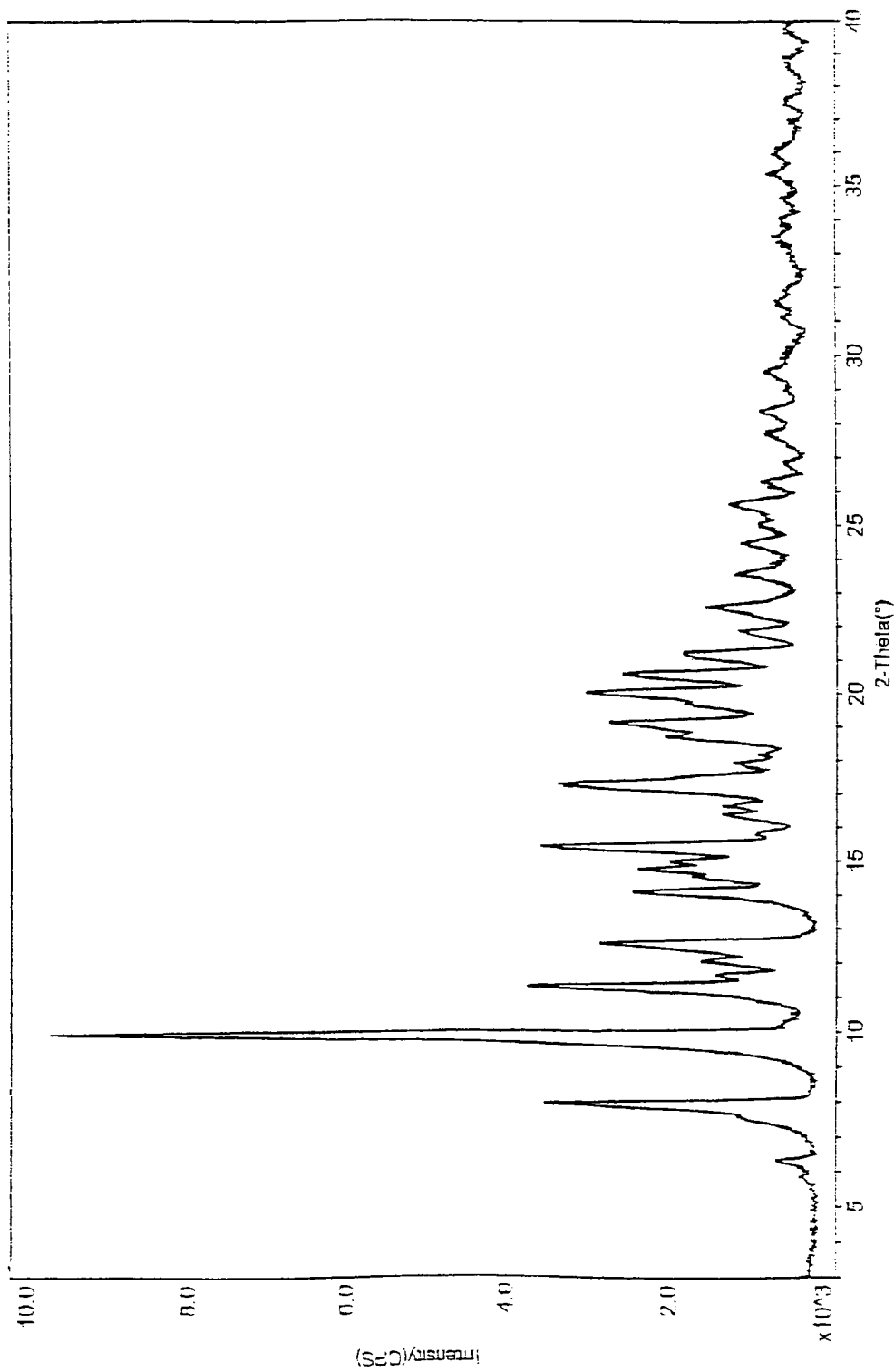
FIG. 1 depicts the X-ray powder diffraction (XRPD) pattern of the crystalline azithromycin monohydrate.

Crystalline azithromycin monohydrate prepared according to the present invention contains from about 5% to about 7% water. The crystalline azithromycin monohydrate is stable, i.e., there is less than 2% (w/w) degradation products present after storage for 3 months under either ambient (room temperature) or accelerated conditions (40° C. and 75% relative humidity).

The process for preparing a crystalline azithromycin monohydrate, comprises the steps of: (a) dissolving azithromycin in a first solution comprising at least about 50% (v/v) of a $C_1$-$C_6$ alcohol; (b) adding the dissolved azithromycin to a second solution comprising at least about 50% (v/v) water to form a precipitate; (c) isolating the precipitate; and (d) drying the isolated precipitate to a water content of about 5% (w/w) to about 7% (w/w).

The azithromycin used in step (a) may include crystalline forms, amorphous forms, syrups, semisolid forms, and the like. Crystalline forms of azithromycin include polymorphs, solvates, clathrates, and the like, and mixtures thereof. Exemplary crystalline forms of azithromycin are azithromycin dihydrate and azithromycin monohydrate. The azithromycin in step (a) may also include crude azithromycin which can be used without purification. Crude azithromycin may be obtained by the procedures set forth in U.S. Pat. No. 4,517,359 (Example 1) or U.S. Pat. No. 4,474,768 (Examples 3-6). Any suitable concentration of azithromycin may be used in step (a). In one embodiment, the azithromycin is used at a concentration that is near the saturation point of azithromycin in the solution. In another embodiment, the azithromycin is used at a concentration of about 0.3 grams/mL.

The first solution in step (a) contains a $C_1$-$C_6$ alcohol. Alcohols encompasse both linear and branched alcohols, such as, methanol, ethanol, n-propanol, isopropanol, 1,2-propanediol, n-butanol, t-butanol, 1,4-butanediol, n-pentanol, or n-hexanol. In one embodiment, the alcohol is ethanol. In another embodiment, the ethanol is present at 50% (v/v) diluted in water. In a third embodiment, ethanol is used as a 95% (v/v) solution.

The first solution in step (a) may be heated to promote dissolution of the azithromycin in the first solution. In one embodiment, step (a) is performed at a temperature from about 30° C. to about the reflux temperature of the solution. In another embodiment, step (a) is performed at a temperature from about 50° C. to about the reflux temperature of the solution. In a third embodiment, step (a) is performed at a temperature from about 70° C. to about the reflux temperature of the solution.

In step (b), the dissolved azithromycin solution is added to the second solution to form a precipitate which contains crystalline azithromycin monohdyrate. The second solution in step (b) contains at least about 50% (v/v) water. In one embodiment, the second solution contains at least about 70% (v/v) water. In another embodiment, the second solution contains at least about 90% (v/v) water. In another embodiment, the second solution contains about 100% (v/v) water.

We have found that when the dissolved azithromycin solution is added to the second solution, the precipitate isolated in step (c) and dried in step (d) contains less than about 0.5% (w/w) $C_1$-$C_6$ alcohol (this percentage of $C_1$-$C_6$ alcohol is significantly lower than the 2% (w/w) obtained when the second solution is added to the dissolved azithromycin solution).

The second solution in step (b) may be used at any suitable quantity. In one embodiment, the vol/vol ratio of first solution in step (a) to second solution in step (b) is about 1:10 to about 10:1. In another embodiment, the vol/vol ratio of first solution to second solution is about 1:5 to about 5:1. In a third embodiment, the vol/vol ratio of first solution to second solution is about 1:2 to about 2:1. In a fourth embodiment, the vol/vol ratio of first solution to second solution is about 1:1. The precipitation of the azithromycin in step (b) may be performed at any suitable temperature. In one embodiment, the precipitation is performed at a temperature of about 0° C. to about 30° C.; in another embodiment, the precipitation is performed at a temperature of about 20° C.

The precipitate formed in step (b) may be isolated using any suitable method. One skilled in the art may optimize the isolation conditions to maximize the yield. Such methods include, but are not limited to, filtration, centrifugation, and decantation. Preferably, the isolating step is performed with filtration. After isolation, the precipitate may be dried (step (d)) using any suitable method. An exemplary drying method is oven drying at atmospheric or reduced pressure. Another exemplary drying method is drying under a stream of gas (nitrogen, air, and the like). The isolated precipitate (step (d)) is dried to a water content of about 5% (w/w) to about 7% (w/w). In one embodiment, the water content of the precipitate is about 5% (w/w) to about 6.5% (w/w); in another embodiment, water content of the precipitate is about 5% (w/w) to about 6% (w/w).

The drying step in step (d) may be performed in stages. To achieve the desired water content, the isolated precipitate may first be dried for a period of time; and then dried for a subsequent period of time. Water content may be conveniently determined at different stages to ensure that a specified water content is achieved. Drying time and conditions may be easily optimized by one skilled in the art. Water content determination is in accordance to U.S. Pharmacopeia (USP) <921> Method I, which is incorporated herein by reference in its entirety.

In a further embodiment, the dissolved azithromycin solution (step (a)) may be filtered prior to precipitation. Filtering the dissolved azithromycin solution removes insoluble contaminants prior to precipitation. Filtration may be performed using diatomaceous earth (e.g., the active ingredient in CELITE® (World Minerals, Inc., Santa Barbara, Calif.). After filtration, the dissolved azithromycin filtrate is collected, and subsequently added into the second solution in order to precipitate the azithromycin (step (b)). If the dissolved azithromycin filtrate is not collected (step (a)), it is allowed to flow directly into the second solution (step (b)). When the dissolved azithromycin filtrate flows directly into the second solution, the dissolved azithromycin solution is kept at a temperature from about 50° C. to about the reflux temperature of the solution.

The precipitate isolated in step (c) may be slurried in water. In one embodiment, the slurry contains at least about 50% (v/v) water. In another embodiment, the slurry contains at least about 70% (v/v) water. In a third embodiment, the slurry contains at least about 90% (v/v) water, while in a fourth embodiment, the slurry contains about 100% water. If the slurry has less than 100% (v/v) water, the remaining volume (up to 100%) is made up by a solvent(s) in which the azithromycin is insoluble. Such solvents may be easily identified by one of ordinary skill in the art. The slurrying step may be performed in any suitable volume. For example, the wt/wt ratio of the isolated precipitate (step (c)) to the total quantity of water may range from about 1:100 to about 1:1. In another embodiment, the ratio may be from about 1:50 to about 1:2; in a third embodiment, the ratio is 1:10 to about 1:3, while in a fourth embodiment, the ratio is about 1:7. The slurrying step may be performed at any suitable temperature, e.g., from about 0° C. to about 30° C., or ambient temperature (e.g., about 20° C. to about 25° C.). The time for the slurrying step may be determined by routine experimentation. Suitable times include, (i) about 30 minutes to about 10 hours, (ii) about 1 hour to about 7 hours, or (iii) about 5 hours. The slurried precipitate may be isolated using any suitable method, e.g., filtration, centrifugation, or decantation.

Crystalline azithromycin monohydrate prepared according to the present invention is stable, i.e., it exhibits less than 2% degradation after storage for at least 3 months at 40° C. and 75% relative humidity. The crystalline azithromycin is non-hygroscopic, i.e., the water content does not change significantly after storage for at least 3 months when stored at 40° C. and 75% relative humidity (non-hydroscopic).

The crystalline azithromycin monohydrate is also substantially free of residual organic solvent, having less than about 0.5% (w/w) $C_1$-$C_6$ alcohol. In one embodiment, the crystalline azithromycin monohydrate contains less than about 0.3% (w/w) $C_1$-$C_6$ alcohol; in another embodiment, the crystalline azithromycin monohydrate contains less than about 0.1% (w/w) $C_1$-$C_6$ alcohol. In a preferred embodiment, the crystalline azithromycin monohydrate prepared according to the methods of the present invention contains less than about 0.1% ethanol.

The crystalline azithromycin monohydrate may be formulated into a pharmaceutical composition. Suitable pharmaceutical compositions include, but are not limited to, those suitable for oral, rectal, parenteral, topical, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterile administration. The pharmaceutical composition may include pharmaceutically acceptable additives, such as excipients, carriers, diluents, stabilizers, plasticizers, binders, glidants, disintegrants, bulking agents, lubricants, colorants, film formers, flavoring agents, preservatives (including antioxidants), dosing vehicles, solvents, additional therapeutic agents, bioavailability enhancers, adjuvants, side-effect suppressing components, buffers, surface active agents, thickeners, and other ingredients as known in the art. Preferably, these additives are pharmaceutically acceptable additives, such as those described in *Remington's, The Science and Practice of Pharmacy*, pp. 858-929 (Gennaro, A. R., ed., 19th edition, 1995, Mack Pub. Co.

The pharmaceutical composition contains one or more pharmaceutical acceptable excipients. The compositions may be presented in unit dosage form and may be prepared by any method known in the art. Such methods include the step of bringing the crystalline azithromycin monohydrate into association with an excipient. In general, the formulations are prepared by uniformly and intimately bringing into association the crystalline azithromycin monohydrate with liquid carriers or finely divided solid carriers or both, and then if necessary shaping the product. Various unit dose and multi-dose containers, e.g., sealed ampules and vials, may be used, as is well known in the art. Oral pharmaceutical compositions may be tablets, pills, capsules, caplets, boluses, powders, granules, elixirs, syrups, or suspensions.

Tablets and pills can additionally be prepared with enteric coatings and other release-controlling coatings. The coating may be colored with a pharmaceutically accepted dye. The amount of dye and other excipients in the coating liquid may vary. The coating liquid generally comprises film-forming polymers such as hydroxy-propyl cellulose, hydroxypropylmethyl cellulose, cellulose ester or ether, in acrylic polymer or a mixture of polymers. The coating solution is generally an aqueous solution that may further comprising propylene glycol, sorbitan monooleate, sorbic acid, fillers such as titanium dioxide, a pharmaceutically acceptable dye. The solid pharmaceutical compositions may include diluents. Diluents for solid compositions include, for example, microcrystalline cellulose (e.g. AVICEL®, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions may include binders, e.g.,acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch.

Disintegrants such as alginic acid, carboxymethylcellulose calcium, carboxymethylcellulose sodium (e.g. AC-DI-SOL®, PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®), or starch may be added to the solid pharmaceutical compositions. Glidants such as, colloidal silicon dioxide, magnesium trisilicate, powdered cellulose, starch, talc and tribasic calcium phosphate may also be added.

Other pharmaceutical additives include: (i) lubricants such as, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate; (ii) flavoring agents and flavor enhancers such as, maltol, vanillin, ethyl vanillin, menthol, citric acid, fumaric acid ethyl maltol, and tartaric acid; and, (iii) pharmaceutically acceptable colorants.

Oral liquid formulations, such as elixirs and solutions, may include carriers and additives, such as water, glycols, oils, alcohols, flavoring agents, preservatives, coloring agents and the like. Parenteral formulations may include, for example, sterile water, solubilizing agents, suspending agents, thickening agents, and preservatives.

Selection of excipients and the amounts to use may be readily determined by formulation scientists based upon experience and consideration of standard procedures and reference works in the field. The solid compositions of the present invention include powders, granulates, aggregates and compacted compositions. The dosages may be conveniently presented in unit dosage form and prepared by any of the methods well known in the pharmaceutical arts. Dosage forms include solid dosage forms like tablets, pills, powders, caplets, granules, capsules, sachets, troches and lozenges.

The invention is illustrated but not limited by the following examples.

EXAMPLE 1

Physical Characterization of Crystalline Azithromycin Monohydrate (A) X-Ray Powder Diffraction Pattern The x-ray powder diffraction (XRPD) pattern of a crystalline azithromycin monohydrate was obtained using a Rigaku X-ray diffractometer Ultima 2200 with a Cu $K_\alpha$ (Ni) radiation source. The samples were run over the range from 5° to 40° with a step size of 0.02° at a rate of 2 steps/second. FIG. 1 depicts a typical x-ray powder diffraction diagram of the crystalline azithromycin monohydrate. The crystalline azithromycin monohydrate is characterized by XRPD peaks at 7.99, 9.94, 11.32, 12.56, 14.74, 15.42, 17.26, 19.12, and 19.98+/−0.2 degrees 2-theta. The relative sizes of the peaks are listed in the following table.

| 2-Theta (°) | Relative Peak Size (%)* |
|---|---|
| 7.99 | 39.6 |
| 9.94 | 100.0 |
| 11.32 | 42.0 |
| 12.56 | 37.5 |
| 14.74 | 34.9 |
| 15.42 | 34.0 |
| 17.26 | 34.6 |
| 19.12 | 29.9 |
| 19.98 | 30.5 |

*assumes the peak at 9.94 to be 100.0%

(B) Near IR Spectroscopy

Figure 2:
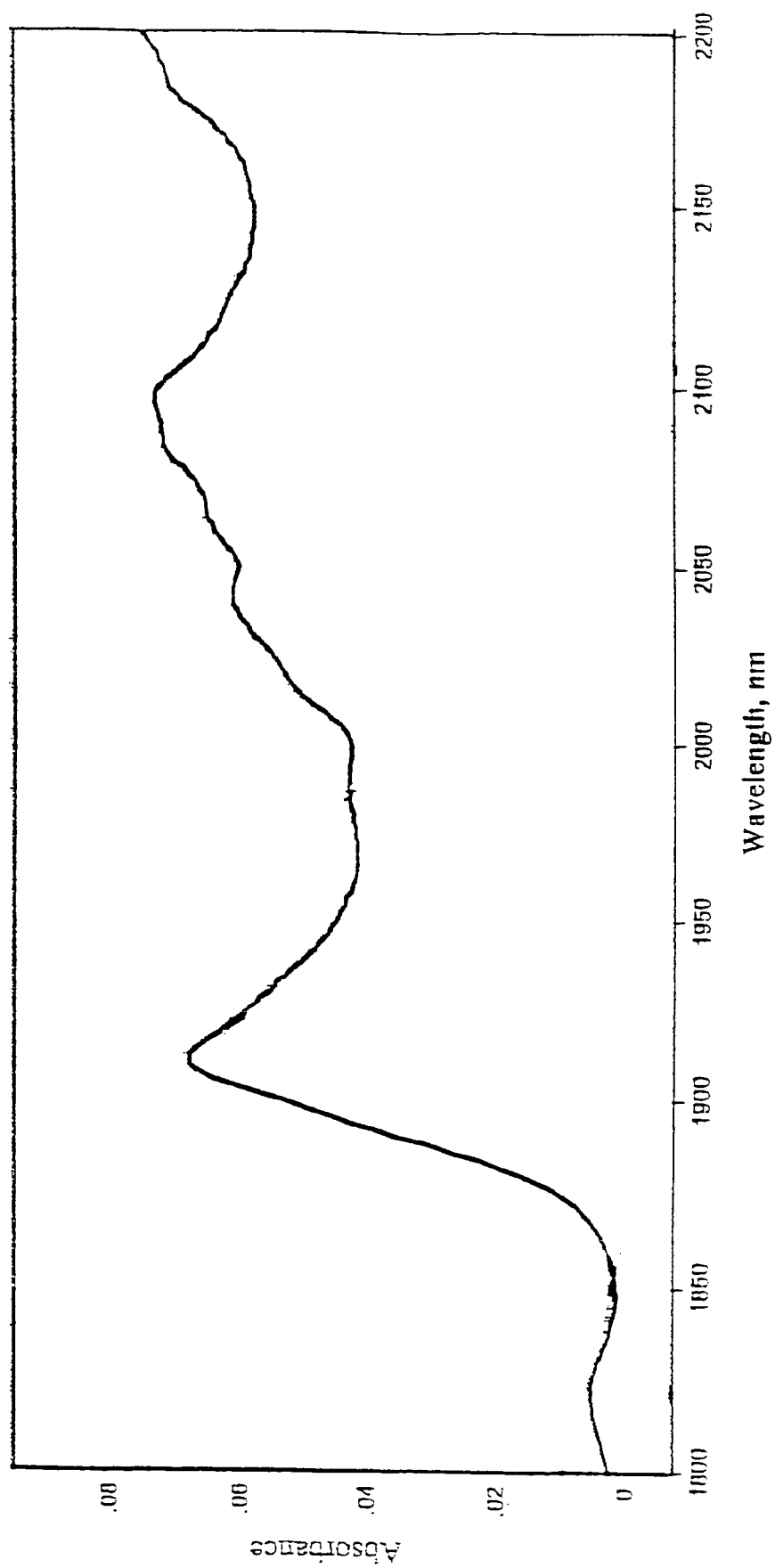
FIG. 2 depicts the near infrared (NIR) spectrum of the crystalline azithromycin monohydrate.

The near infrared (NIR) spectrum of a crystalline azithromycin monohydrate was obtained using a TOSS NIR Systems 5000 Rapid Content Sampler: (i) Wavelength range: 1100-2500 nm; (ii) Wavelength accuracy: 0.3 nm; (iii) Wavelength repeatability: 0.010 nm; (iv) Spectral bandwidth: 10-1 nm; (v) Scan rate: 1.8 scans/second; (vi) Number of scans: 64; (vii) Background: $TiO_2$ diffusion plate; and, (viii) Wavelength calibration: polystyrene film. Diffuse Reflection Spectra were measured of the samples as powders. NIRSystems digital spectral files were converted to GRAMS (Galactic Industries Corp., Salem N.H.) *.spc for display. FIG. 2 depicts a typical NIR spectrum of the crystalline azithromycin monohydrate.

EXAMPLE 2

Preparation of Crude Azithromycin

Azaerythromycin (100 kg) (Ercros Ind., Madrid, Spain) and 95% ethanol (500 L) were combined to form a mixture in a 1,000-L reaction vessel. The mixture was then stirred. Paraformaldehyde (10.4 kg) and formic acid (15 kg) were added, and the mixture was heated at a reflux temperature (i.e., 78° C.) for about 4 hours.

When thin-layer chromatography (TLC) indicated the disappearance of azaerythromycin, about 200 L of ethanol was removed by distillation under vacuum. At about 25-30° C., water (300 kg) and 25% ammonium hydroxide (40 kg) were added to bring the pH to above 9. Then, more water (300 kg) was added. The mixture was further stirred at room temperature for about 6 hours. The precipitate was filtered and washed with water, providing about 105 kg of crude, wet azithromycin (contained 24.74% water (w/w)).

EXAMPLE 2

Methods (A) Purity Determination (i) Chromatographic Conditions—The purity of a crystalline azithromycin monohydrate sample was determined using a high performance liquid chromatography (HPLC) instrument with a variable wavelength detector. The chromatographic conditions were: (i) Column—Xterra RP-18, endcapped 5 μm, 250×4.6 mm or equivalent; (ii) Flow Rate—1.0 mL/min; (iii) Column temperature—28° C.; (iv) Detection—UV at 215 nm; (v) Injection volume—20 μL; (vi) Run time—30 min; and, (vii) Mobile phase,Borate buffer pH=9.5: Acetonitrile (1:1, v/v). The mobile phase was prepared by adding NaOH (5N) to a solution of boric acid (about 1.2 grams) in water (1,000 mL; HPLC grade) to obtain a pH of 9.5.

(ii) Standard Solution for Purity Determination—A standard solution for purity determination was prepared by dissolving azithromycin monohydrate (about 50 mg, accurately weighed), in sufficient acetonitrile to fill a 25 mL volumetric flask. The azithromycin monohydrate used in the standard solution was prepared according to the procedure set forth in U.S. Pat. No. 6,268,489. The prepared azithromycin monohydrate had a water content of 3.8%, and a purity of 98.6%.

(iii) Preparation of Crystalline Azithromycin Monohydrate Sample Solution—A crystalline azithromycin monohydrate sample solution was prepared by transferring approximately 50 mg of the crystalline azithromycin monohydrate sample to be assayed into a 25 mL volumetric flask and diluting to volume with acetonitrile.

(iv) HPLC Protocol—The retention time of azithromycin was about 20 minutes. The retention time of azaerythromycin was about 13 minutes. Six replicates of the standard solution for determination of impurities, and 5 replicates of the standard solution for purity determination were injected into the HPLC system. The relative standard deviation of 5 replicate injections of the standard solution for purity determination was not more than 2.0%. The relative standard deviation of 6 replicate injections of the standard solution for determination of impurities was not more than 5.0%. If necessary, the mobile phase composition and/or flow rate were adjusted to meet the chromatographic parameters. The limit of detection for azaerythromycin was 0.04%. The limit of quantitation for azaerythromycin was 0.04%. The limit of detection for azithromycin was 0.04%. The limit of quantitation for azithromycin was 0.05%.

(v) Calculation of Purity $$\% \text{ Purity(calculated on anhydrous basis)} = \frac{Wst \times Ssm \times Pst \times 100}{Sst \times Wsm \times (100 - Msm)}$$

The terms are defined as follows: (i) Wst=Weight of standard in mg; (ii) Wsm=Weight of sample in mg; (iii) Ssm=Peak area of azithromycin obtained from sample solution; (iv) Sst=Average peak area of azithromycin obtained from standard solution for purity determination; (v) Pst=Purity of azithromycin standard in percent; and (vi) Msm=Water content of sample in percent.

(B) Determination of Ethanol Content of Crystalline Azithromycin Monohydrate

Analysis was performed on a gas chromatograph (GC) with a FID detector and a headspace sampler. The procedure may be adapted to determine the content of other organic solvents, including other $C_1$-$C_6$ alcohols.

(i) GC Conditions—(i) Column type—cyanomethyl phenyl sil; (ii) Column dimensions—75 m, 0.53 mm, 1.0 μm (megabore column); (iii) Inlet—purged packed, aux 4 pressure controlled; (iv) Inlet temperature—200° C.; (iv) Carrier gas—He, constant flow of 10.0 mL/min; (v) Vial pressure 15 psi; (vi) Detector temperature—250° C.; (vii) Detector constant flow & makeup flow—30.0 mL/min; (viii) Oven initial temperature—70° C. (for 7 min); (ix) Oven rate—100° C./min; and, (x) Final oven temperature—220° C. (for 5 min).

(ii) Headspace Sampler Conditions—(i) Sample oven temperature—90° C.; (ii)Sample valve (loop) temperature—

100° C.; (iii) Transfer line temperature—120° C.; (iv) GC cycle time—30 min, (v) Sample equilibration time—30 min; (vi) Vial pressurization time—0.20 min; (vii) Loop fill time—0.15 min; (viii) Loop equilibration time—0.05 min; (ix) Sample injection time—0.50 min; (x) Oven stabilization time—1.0 min; and (xi) Shaking—high agitation.

(iii) Preparation of Ethanol Standard Solution—The standard solution was prepared in two steps. First, ethanol (about 800 mg) was transferred into a 100-mL volumetric flask, and diluted to volume with N,N-dimethylformamide. Second, 2.5 mL of the resulting solution was transferred into a 100-mL volumetric flask, and diluted to volume with N,N-dimethylformamide (100 mL).

(iv) Preparation of Crystalline Azithromycin Monohydrate Sample Solution—Crystalline azithromycin monohydrate (about 200 mg, accurately weighed) was transferred into a 20-mL headspace vial. N.N-dimethylformamide (5 mL) was added, and the vial was sealed immediately with a Teflon-line septum and crimp cap.

(v) GC Protocol—The standard solution, diluent (N.N-dimethylformamide), and the crystalline azithromycin monohydrate sample solution vials were injected into the chromatograph. In the diluent chromatogram, a flat baseline within the retention time window of each solvent peak was obtained. The peak area of each sample was obtained using an integration device.

(vi) Calculation of Ethanol Content $$\text{Ethanol(ppm)} = \frac{Wst \times Ssm \times 1250}{Sst \times Wsm}$$

The terms are defined as follows: (i) Wst=Weight of Ethanol standard in mg; (ii) Ssm=Peak area of Ethanol obtained from sample solution; (iii) Sst=Average peak area of Ethanol obtained from standard solution; and (iv) Wsm=Weight of sample in mg.

EXAMPLE 3

Preparation of Crystalline Azithromycin Monohydrate

The crude azithromycin prepared in Example 1 (105 kg) was dissolved in about 304 L ethanol (95%) at about 70° C. in a 800 L reaction vessel. The solution was then hot filtered through about 1 kg of Celite®, and the filtrate was allowed to directly flow into about 304 kg of water in a 1,000-L reaction vessel. During the addition, the water temperature was maintained at about 20° C. The resulting slurry was stirred for about 5 hours. The precipitate was filtered and washed with water, providing about 109.4 kg of wet precipitate (contained 35.42% water (w/w)).

The wet precipitate was slurried vigorously in about 700 L of water in a 1,000-L reaction vessel for about 5 hours at room temperature. The slurry was filtered, washed with water, and dried in stages to provide about 68.2 kg of crystalline azithromycin monohydrate.

The water content, ethanol content, purity, stability, hygroscopicity, and other parameters are presented in Tables 1 and 2.

Table 1 shows that the crystalline azithromycin monohydrate was stable and non-hygroscopic for 3 months when stored at 25° C. and 60% relative humidity. Table 2 shows that the crystalline azithromycin monohydrate was stable and non-hygroscopic for 3 months when stored at 40° C. and 75% relative humidity.

TABLE 1

Crystalline azithromycin monohydrate stored under ambient conditions (25° C. and 60% relative humidity)

| | Time (Months) | |
|---|---|---|
| | 0 | 3 |
| Appearance | White crystalline powder | White crystalline powder |
| pH | 10.4 | 10.2 |
| Ethanol content (%) | 0.0601% (601 ppm) | not tested |
| Water content (%) | 5.9 | 5.8 |
| Azaerythromycin (%) | 0.3 | 0.3 |
| Other Impurities | RRT = 0.23, % = 0.10 | RRT = 0.10, % = 0.20 |
| | RRT = 0.26, % = 0.20 | RRT = 0.24, % = 0.10 |
| | RRT = 0.34, % = 0.10 | RRT = 0.35, % = 0.10 |
| | RRT = 0.42, % = 0.30 | RRT = 0.43, % = 0.30 |
| | RRT = 0.45, % = 0.07 | RRT = 0.46, % = 0.07 |
| | RRT = 0.48, % = 0.20 | RRT = 0.49, % = 0.20 |
| | RRT = 1.45, % = 0.05 | RRT = 0.81, % = 0.10 |
| | RRT = 1.50, % = 0.20 | RRT = 0.84, % = 0.08 |
| | RRT = 1.56, % = 0.10 | RRT = 1.50, % = 0.20 |
| | | RRT = 1.55, % = 0.10 |
| Total Impurities (%) | 1.60 | 1.80 |
| Purity (%) | 100.10 | 98.70 |

RRT = Relative retention time

TABLE 2

Crystalline azithromycin monohydrate stored under accelerated conditions (40° C. and 75% relative humidity)

| | Time (Months) | | | |
|---|---|---|---|---|
| | 0 | 1 | 2 | 3 |
| Appearance | White crystalline powder | White crystalline powder | White crystalline powder | White crystalline powder |
| pH | 10.4 | 10.0 | 10.3 | 10.3 |
| Ethanol content (%) | 0.0601% (601 ppm) | not tested | not tested | not tested |
| Water content (%) | 5.9 | 5.9 | 5.8 | 5.7 |
| Azaerythromycin (%) | 0.3 | 0.4 | 0.3 | 0.3 |
| Other Impurities (RRT, %) | RRT = 0.23, % = 0.10 | 0.23, 0.10 | 0.23, 0.10 | 0.14, 0.20 |
| | RRT = 0.26, % = 0.20 | 0.26, 0.20 | 0.25, 0.20 | 0.24, 0.10 |
| | RRT = 0.34, % = 0.10 | 0.35, 0.10 | 0.34, 0.10 | 0.35, 0.20 |
| | | 0.38, 0.05 | 0.42, 0.40 | 0.43, 0.40 |
| | RRT = 0.42, % = 0.30 | 0.43, 0.30 | 0.45, 0.05 | 0.46, 0.07 |
| | | 0.46, 0.08 | 0.48, 0.20 | 0.49, 0.20 |
| | RRT = 0.45, % = 0.07 | 0.48, 0.20 | 1.50, 0.20 | 0.81, 0.06 |
| | | 1.50, 0.20 | 1.56, 0.10 | 0.85, 0.05 |
| | RRT = 0.48, % = 0.20 | 1.56, 0.20 | | 1.50, 0.20 |
| | RRT = 1.45, % = 0.05 | | | 1.55, 0.08 |
| | RRT = 1.50, % = 0.20 | | | |
| | RRT = 1.56, % = 0.10 | | | |
| Total Impurities (%) | 1.60 | 1.80 | 1.70 | 1.90 |
| Purity (%) | 100.10 | 101.00 | 99.50 | 98.10 |

RRT = Relative retention time

The hygroscopicity of a crystalline azithromycin monohydrate was determined by monitoring its water content during storage. Specifically, the water content of the crystalline azithromycin monohydrate was determined at time zero and at various times thereafter during storage (e.g., 1, 2, and 3 months) under ambient conditions and accelerated conditions. As shown in Tables 1 and 2, the water content of crystalline azithromycin monohydrate remained substantially unchanged after storage for 3 months under ambient conditions or accelerated conditions.

Numerous references, including patents and various publications, are cited and discussed in the description of this invention. The citation and discussion of such references is provided merely to clarify the description of the present invention and is not an prior art admission to the invention described herein. All references cited and discussed in this specification are incorporated herein by reference in their entirety.

What is claimed is:

1. A process for preparing a crystalline azithromycin monohydrate, comprising the steps of:
   (a) dissolving azithromycin in a first solution comprising 95% (v/v) of ethanol at 70° C.;
   (b) adding the dissolved azithromycin to a second solution comprising about 100% water to form a precipitate;
   (c) isolating the precipitate; and,
   (d) drying the isolated precipitate and providing crystalline azithromycin monohydrate having a water content of about 5% (w/w) to about 7% (w/w).

2. The process of claim 1, wherein the crystalline azithromycin monohydrate is characterized by less than 2% (w/w) degradation after storage for at least about 3 months at 40° C. and 75% relative humidity.

3. The process of claim 1, wherein the crystalline azithromycin monohydrate is characterized by less than 4% change in the water content after storage for at least about 3 months at 40° C. and 75% relative humidity.

4. The process of claim 1, wherein step (c) is performed at a temperature of about 0° C. to about 30° C.

5. The process of claim 1, wherein step (d) is performed by filtration.

6. The process of claim 1, wherein the isolated precipitate (step (d)) is dried to a water content of about 5% (w/w) to about 6.5% (w/w).

7. A process for preparing a crystalline azithromycin monohydrate, comprising the steps of:
   (a) dissolving azithromycin in a 95% (v/v) solution of ethanol at about 70° C.;
   (b) filtering the dissolved azithromycin through diatomaceous earth;
   (c) adding the dissolved azithromycin to water to form crystalline azithromycin monohydrate;
   (d) isolating crystalline azithromycin monohydrate;
   (e) slurrying the isolated crystalline azithromycin monohydrate; and,
   (f) drying the isolated crystalline azithromycin monohydrate to a water content of about 5% (w/w) to about 7% (w/w).

* * * * *